(12) United States Patent
Chen et al.

(10) Patent No.: US 8,106,243 B2
(45) Date of Patent: Jan. 31, 2012

(54) PROCESS FOR PRODUCING CYCLOHEXYLBENZENE

(75) Inventors: Tan-Jen Chen, Kingwood, TX (US); Jane C. Cheng, Bridgewater, NJ (US); Francisco M. Benitez, Houston, TX (US); Terry E. Helton, Bethlehem, PA (US); Jon E. Stanat, Westhampton Beach, NY (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/933,709

(22) PCT Filed: Feb. 23, 2009

(86) PCT No.: PCT/US2009/034823
§ 371 (c)(1),
(2), (4) Date: Sep. 21, 2010

(87) PCT Pub. No.: WO2009/134516
PCT Pub. Date: Nov. 5, 2009

(65) Prior Publication Data
US 2011/0021841 A1  Jan. 27, 2011

Related U.S. Application Data

(60) Provisional application No. 61/049,530, filed on May 1, 2008.

(51) Int. Cl.
*C07C 45/53* (2006.01)
*C07C 37/08* (2006.01)
*C07C 2/68* (2006.01)

(52) U.S. Cl. .................. 568/346; 568/631; 585/467

(58) Field of Classification Search .................. 568/346, 568/361, 798; 585/467
See application file for complete search history.

(56) References Cited

U.S. PATENT DOCUMENTS

| | | | |
|---|---|---|---|
| 3,197,399 A | 7/1965 | Wight et al. |
| 3,201,356 A | 8/1965 | Kress et al. |
| 3,347,945 A | 10/1967 | Slaugh |
| 3,390,101 A | 6/1968 | Csicsery |
| 3,412,165 A | 11/1968 | Slaugh et al. |
| 3,760,017 A | 9/1973 | Arkell et al. |
| 3,760,018 A | 9/1973 | Suggitt et al. |
| 3,760,019 A | 9/1973 | Crone, Jr. et al. |
| 3,784,617 A | 1/1974 | Suggitt et al. |
| 3,784,618 A | 1/1974 | Suggitt et al. |
| 3,839,477 A | 10/1974 | Suggitt et al. |
| 3,864,421 A | 2/1975 | Suggitt |
| 3,957,687 A | 5/1976 | Arkell et al. |
| 4,021,490 A | 5/1977 | Hudson |
| 4,094,918 A | 6/1978 | Murtha et al. |
| 4,122,125 A | 10/1978 | Murtha et al. |
| 4,152,362 A | 5/1979 | Murtha |
| 4,177,165 A | 12/1979 | Murtha et al. |
| 4,206,082 A | 6/1980 | Murtha et al. |
| 4,219,689 A | 8/1980 | Murtha |
| 4,268,699 A | 5/1981 | Murtha et al. |
| 4,329,531 A | 5/1982 | Murtha et al. |
| 4,380,683 A | 4/1983 | Dolhyj et al. |
| 4,439,409 A | 3/1984 | Puppe et al. |
| 4,447,554 A | 5/1984 | Murtha et al. |
| 4,826,667 A | 5/1989 | Zones et al. |
| 4,954,325 A | 9/1990 | Rubin et al. |
| 4,962,250 A | 10/1990 | Dessau et al. |
| 5,037,538 A | 8/1991 | Chin et al. |
| 5,053,571 A | 10/1991 | Makkee |
| 5,108,969 A | 4/1992 | Del Rossi et al. |
| 5,146,024 A | 9/1992 | Reed |
| 5,236,575 A | 8/1993 | Bennett et al. |
| 5,250,277 A | 10/1993 | Kresge et al. |
| 5,292,976 A | 3/1994 | Dessau et al. |
| 5,334,795 A | 8/1994 | Chu et al. |
| 5,362,697 A | 11/1994 | Fung et al. |
| 5,384,296 A | 1/1995 | Tsao |
| 5,488,194 A | 1/1996 | Beck et al. |
| 5,554,274 A | 9/1996 | Degnan et al. |
| 5,557,024 A | 9/1996 | Cheng et al. |
| 5,705,729 A | 1/1998 | Huang |
| 6,037,513 A | 3/2000 | Chang et al. |
| 6,077,498 A | 6/2000 | Diaz Cabanas et al. |
| 6,133,470 A | 10/2000 | Beck et al. |
| 6,489,529 B1 | 12/2002 | Cheng et al. |
| 6,504,070 B2 | 1/2003 | Matsumoto et al. |
| 6,506,953 B1 | 1/2003 | Cheng et al. |

(Continued)

FOREIGN PATENT DOCUMENTS

| | | |
|---|---|---|
| EP | 0 293 032 | 11/1988 |
| EP | 0 338 734 | 10/1989 |
| JP | 2005-342644 | 12/2005 |
| WO | 95/31421 | 11/1995 |
| WO | 97/17290 | 5/1997 |
| WO | 01/53236 | 7/2001 |
| WO | 01/74767 | 11/2001 |
| WO | 2005/118476 | 12/2005 |
| WO | WO 2009/021604 | 2/2009 |
| WO | 2009/038900 | 3/2009 |

OTHER PUBLICATIONS

Borodina, I.B. et al., "Hydroalkylation of Benzene and Ethylbenzene over Metal Containing Zeolite Catalysts", Microporous and Mesoporous Materials, 2007, vol. 105, pp. 181-188.

(Continued)

*Primary Examiner* — Sikarl Witherspoon
(74) *Attorney, Agent, or Firm* — Jamie Sullivan

(57) ABSTRACT

In a process for producing cyclohexylbenzene, benzene and hydrogen are contacted with a catalyst under hydroalkylation conditions to produce an effluent containing cyclohexylbenzene. The catalyst comprises a composite of a molecular sieve, an inorganic oxide different from said molecular sieve and at least one hydrogenation metal, wherein at least 50 wt % of said hydrogenation metal is supported on the inorganic oxide and the inorganic oxide has an average particle size less than 40 μm (microns).

25 Claims, No Drawings

U.S. PATENT DOCUMENTS

| | | | |
|---|---|---|---|
| 6,730,625 | B1 | 5/2004 | Chang et al. |
| 6,781,025 | B2 | 8/2004 | Dandekar et al. |
| 6,936,744 | B1 | 8/2005 | Cheng et al. |
| 7,488,861 | B2 | 2/2009 | Boyer et al. |
| 7,579,511 | B1 | 8/2009 | Dakka et al. |
| 2003/0083527 | A1 | 5/2003 | Kuhnle et al. |
| 2004/0092757 | A1 | 5/2004 | Oguchi et al. |
| 2005/0158238 | A1 | 7/2005 | Tatsumi et al. |
| 2008/0027256 | A1 | 1/2008 | Roth et al. |
| 2008/0027259 | A1 | 1/2008 | Roth et al. |
| 2008/0045768 | A1 | 2/2008 | Roth et al. |

OTHER PUBLICATIONS

Fan, W. et al. "Synthesis and Catalytic Properties of a New Titanosilicate Molecular Sieve with the Structure Analogous to MWW-type Lamellar Precursor" Journal of Catalyst, 2006, vol. 243, pp. 183-191.

Wu, P. et al., "Methodology for Synthesizing Crystalline Metallosilicates with Expanded Pore Windows Through Molecular Alkoxysilylation of Zeolitic Lamellar Precursors" Journal of American Chemical Soc., 2008, vol. 130, pp. 8178-8187.

Lawton, S.L. et al. "Zeolite MCM-49: A Three-Dimensional MCM-22 Analogue Synthesized by in Situ Crystallization", Journal of Physical Chemistry, 1996, vol. 100, No. 9, pp. 3788-3798.

Ruan, J. "Structure Elucidation of the Highly Active Titanosilicate Catalyst Ti-YNU-1" Angew. Chem. Int. Ed., 2005, vol. 44, pp. 6719-6723.

Se-Young, K. et al., "Structural Evolution of B-MCM-36 and B-ITQ-2 from B-MCM-22" Bull. Korean Chem. Society, 2006, vol. 27, No. 10, pp. 1693-1696.

Slaugh, L.H. et al., "Hydrodimerization of Benzene to Phenylcyclohexane over Supported Transition Metal Catalysts" Journal of Catalysis, 1969, vol. 13, pp. 385-396.

Maheshwari, S. et al., "Layer Structure Preservation During Swelling, Pillaring, and Exfoliation of a Zeolite Precursor" Journal of American Chemical Soc., 2008, vol. 130, No. 4, pp. 1507-1516.

Zhicheng L. et al, "Static Synthesis of High-Quality MCM-22 Zeolite with High $SiO_2/Al_2O_3$ Ratio" Chinese Science Bull, 2004, vol. 49, No. 6, pp. 556-561.

US 8,106,243 B2

PROCESS FOR PRODUCING CYCLOHEXYLBENZENE

CROSS-REFERENCE TO RELATED APPLICATIONS

This application is a National Stage Application of International Application No. PCT/US2009/034823 filed Feb. 23, 2009, which claims priority from U.S. Ser. No. 61/049,530 filed May 1, 2008, both of which are incorporated herein by reference.

FIELD OF THE INVENTION

The present invention relates to a process for producing cyclohexylbenzene optionally and for converting the resultant cyclohexylbenzene into phenol and cyclohexanone.

BACKGROUND

Phenol is an important product in the chemical industry and is useful in, for example, the production of phenolic resins, bisphenol A, ϵ-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene.

Thus, a process that uses higher alkenes instead of propylene as feed and coproduces higher ketones, such as cyclohexanone, rather than acetone may be an attractive alternative route to the production of phenols. For example, there is a growing market for cyclohexanone, which is used as an industrial solvent, as an activator in oxidation reactions and in the production of adipic acid, cyclohexanone resins, cyclohexanone oxime, caprolactam and nylon 6.

It is known from U.S. Pat. No. 5,053,571 that cyclohexylbenzene can be produced by contacting benzene with hydrogen in the presence of a catalyst comprising ruthenium and nickel supported on zeolite beta and that the resultant cyclohexylbenzene can be processed in two steps to cyclohexanone and phenol. The hydroalkylation reaction is carried out at a liquid hourly space velocity (LHSV) ranging from 1 to 100, a reaction pressure ranging from 100 to 1000 kPa, a hydrogen feed rate ranging from 0.2 to 6 mole per mole of feedstock per hour, and a reaction temperature ranging from 100 to 300° C.

In addition, U.S. Pat. No. 5,146,024 discloses that benzene can be reacted with hydrogen in the presence of carbon monoxide and a palladium-containing zeolite X or Y to produce cyclohexylbenzene, which can then be converted in high yield to phenol and cyclohexanone by autooxidation with subsequent acid treatment. The hydroalkylation reaction is carried out at a liquid hourly space velocity (LHSV) of the benzene feed of about 1 to about 100 hr$^{-1}$, a total reaction pressure of about 345 to about 10,350 kPa, a molar ratio of $H_2$ to benzene of about 0.1:1 to about 10:1, a molar ratio of carbon monoxide to $H_2$ of about 0.01:1 to about 0.3:1, and a temperature of about 100 to about 250° C.

Further, U.S. Pat. No. 6,037,513 discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. The catalyst may also contain a binder and/or matrix and in the Examples the catalyst is produced by impregnating an extrudate of the MCM-22 family molecular sieve and an alumina binder with an aqueous solution of a salt of the hydrogenation metal using incipient wetness impregnation. The '513 patent also discloses that the resultant cyclohexylbenzene can be oxidized to the corresponding hydroperoxide and the peroxide decomposed to the desired phenol and cyclohexanone.

In our co-pending U.S. Patent Application Ser. No. 60/964,874, filed Aug. 15, 2007, we have described a process for producing cyclohexylbenzene, the process comprising contacting benzene and hydrogen with a catalyst under hydroalkylation conditions to produce an effluent containing cyclohexylbenzene, the catalyst comprising a composite of a molecular sieve, an inorganic oxide different from said molecular sieve and at least one hydrogenation metal, wherein at least 50 wt % of said hydrogenation metal is supported on the inorganic oxide. By providing at least the majority of the hydrogenation metal on the inorganic oxide support rather than the molecular sieve, it is found that the activity of the catalyst and its selectivity to cyclohexylbenzene and dicyclohexylbenzene are increased.

In the Example disclosed in U.S. Patent Application Ser. No. 60/964,874, the inorganic oxide employed as the support for the hydrogenation metal was CATALOX SBa alumina, which has an average particle size of about 45 μm (microns). According to the present invention, it has now been found that the benzene hydroalkylation activity of a bifunctional catalyst, in which some or all of the hydrogenation metal is supported on an inorganic oxide separate from the molecular sieve, can be enhanced if the inorganic oxide is selected so as to have an average particle size less than 40 μm (microns). Moreover the increase in activity is obtained without significant loss in the selectivity of the catalyst to cyclohexylbenzene and dicyclohexylbenzene, which is desirable since any dicyclohexylbenzene can be readily transalkylated with additional benzene to produce further cyclohexylbenzene product.

SUMMARY

In one aspect, the invention resides in a process for producing cyclohexylbenzene, the process comprising contacting benzene and hydrogen with a catalyst under hydroalkylation conditions to produce an effluent containing cyclohexylbenzene, the catalyst comprising a composite of a molecular sieve, an inorganic oxide different from said molecular sieve and at least one hydrogenation metal, wherein at least 50 wt % of said hydrogenation metal is supported on the inorganic oxide and the inorganic oxide has an average particle size less than 40 μm (microns).

Conveniently, said inorganic oxide has an average particle size less than 20 μm, such as less than 10 μm, for example less than 5 μm. For example, the average particle size of the inorganic oxide is in the range of from 0.01 to 30 μm, or from 0.02 to less than 20 μm, such as from 0.05 to less than 10 μm or from 0.05 to 5 μm.

As used herein, the term "average particle size" means the mean volume diameter of the inorganic oxide particles, that is, the mean diameter (in μm) of the volume distribution of the particles, which represents the centre of gravity of the distribution. An instrument useful for measuring this average particle size of the inorganic oxide employed in accordance with the invention is a Microtrac S-3000 laser particle sizing analyzer available from Microtrac, Inc. (a unit of Nikkiso) of Largo, Fla., USA. Such analyzer employs software that reduces particle sizes to effective spherical diameters, and measures, the particle size as mean volume (MV) diameter.

Conveniently, the inorganic oxide comprises an oxide of at least one element of Groups 2, 4, 13 and 14 of the Periodic Table of Elements, such as alumina and/or titania and/or zirconia.

Conveniently, at least 75 wt %, such as substantially all (eg at least 95 wt % or 98 wt % or 99 wt %), or even 100 wt % of said hydrogenation metal is supported on the inorganic oxide.

Conveniently, the at least one hydrogenation metal is applied to the inorganic oxide before the inorganic oxide is composited with the molecular sieve. In one embodiment, the catalyst is produced by depositing the at least one hydrogenation metal on the inorganic oxide and then co-pelletizing a mixture of the metal-containing inorganic oxide and the molecular sieve. In another embodiment, the catalyst is produced by depositing the at least one hydrogenation metal on the inorganic oxide and then co-extruding a mixture of the metal-containing inorganic oxide and the molecular sieve.

Conveniently, the molecular sieve has an average pore size of at least $7\times10^{-10}$ m (7 Angstrom) and typically is selected from zeolite beta, zeolite X, zeolite Y, mordenite and a molecular sieve of the MCM-22 family.

Conveniently, the molecular sieve is an aluminosilicate and the molar ratio of the aluminum in the molecular sieve to the hydrogenation metal is from about 1.5 to about 1500, such as from about 100 to about 500.

Conveniently, the at least one hydrogenation metal is selected from palladium, ruthenium, nickel, zinc, tin and cobalt, especially palladium.

Conveniently, the hydroalkylation conditions include a temperature of about 100 to about 400° C. and/or a pressure of about 100 to about 7000 kPaa. In one embodiment, the molar ratio of hydrogen to benzene in said contacting is from about 0.15:1 to about 15:1.

In another aspect, the invention resides in a method for coproducing phenol and cyclohexanone, the method comprising producing cyclohexylbenzene by the process described herein, oxidizing the cyclohexylbenzene to produce cyclohexylbenzene hydroperoxide and cleaving the cyclohexylbenzene hydroperoxide to produce phenol and cyclohexanone. In a further embodiment, the cyclohexanone may be dehydrogenated to produce further phenol.

DETAILED DESCRIPTION OF THE EMBODIMENTS

Described herein is a process for the hydroalkylation of benzene to produce cyclohexylbenzene and, in a preferred embodiment of the invention, the conversion of the cyclohexylbenzene in a second step to cyclohexanone and phenol. Insofar as the hydroalkylation process produces dicyclohexylbenzene in addition to the desired monocyclohexylbenzene product, the process can include the further step of transalkylating the dicyclohexylbenzene with additional benzene to produce additional monocyclohexylbenzene product.

Benzene Hydroalkylation

The present process (which comprises the first process step in the above-mentioned preferred embodiment) involves contacting benzene with hydrogen under hydroalkylation conditions and in the presence of a novel hydroalkylation catalyst whereby the benzene undergoes the following reaction:

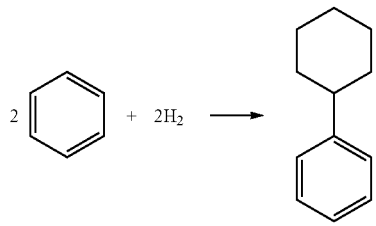

Competing reactions include the complete saturation of the benzene to produce cyclohexane, dialkylation to produce dicyclohexylbenzene and reorganization/alkylation reactions to produce impurities, such as methylcyclopentylbenzene. Although dicyclohexylbenzene can be transalkylated to produce additional monocyclohexylbenzene product, conversion to cyclohexane represents loss of valuable feed, whereas impurities such as methylcyclopentylbenzene (MCPB) are particularly undesirable since the boiling point of MCPB is very close to that of cyclohexylbenzene (CHB) and hence it is very difficult to separate MCPB from CHB, which is the desired product from the hydroalkylation reaction.

Any commercially available benzene feed can be used in the hydroalkylation step, but preferably the benzene has a purity level of at least 99 wt %. Similarly, whereas the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm by weight, water and/or less than 100 ppm, such as less than 30 ppm, for example less than 3 ppm by weight, sulfur and/or less than 10 ppm, such as less than 1 ppm, for example less than 0.1 ppm by weight, nitrogen.

The hydroalkylation reaction can be conducted in a wide range of reactor configurations including fixed bed, slurry reactors, and/or catalytic distillation towers. Suitable reaction temperatures are between about 100° C. and about 400° C., such as between about 125° C. and about 250° C. Suitable reaction pressures are between about 100 and about 7,000 kPaa, such as between about 500 and about 5,000 kPaa. Suitable values for the molar ratio of hydrogen to benzene are between about 0.15:1 and about 15:1, such as between about 0.4:1 and about 4:1.

The novel catalyst employed in hydroalkylation reaction is a composite of a molecular sieve, an inorganic oxide different from the molecular sieve and a hydrogenation metal. In particular, the inorganic oxide is selected so as to have an average particle size less than 40 µm, generally less than 20 µm, such as less than 10 µm for example less than 5 µm. Preferably the average particle size of the inorganic oxide is in the range of from 0.01 to 30 µm or from 0.02 to less than 20 µm such as from 0.05 to less than 10 or 5 µm. Moreover, at least 50 wt % of the hydrogenation metal is supported on the inorganic oxide rather than on the molecular sieve. In particular, it is found that by supporting the hydrogenation metal on a small particle size inorganic oxide, the activity of the catalyst is increased as compared with an equivalent catalyst in which the hydrogenation metal is supported on a larger (>40 µm) particle size inorganic oxide. In addition, it is found that this improvement in activity is achieved without significant loss in the selectivity of the catalyst to the desired products, cyclohexylbenzene and dicyclohexylbenzene Generally, the molecular sieve employed in the present hydroalkylation process has an average pore size of at least $7\times10^{-10}$ m (7 Angstrom) and conveniently is selected from zeolite beta, zeolite X, zeolite Y, mordenite and a molecular sieve of the MCM-22 family. Zeolite beta and its synthesis are disclosed in, for example, U.S. Pat. No. 3,308,069.

The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures of any two or more thereof. Preferably, the molecular sieve is selected from (a) MCM-49, (b) MCM-56 and (c) isotypes of MCM-49 and MCM-56, such as ITQ-2.

The inorganic oxide employed in the hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, or zirconia. Such oxides may be used in admixture. As used herein, the numbering scheme for the Periodic Table Groups is as disclosed in Chemical and Engineering News, 63(5), 27 (1985).

Similarly, any known hydrogenation metal can be employed in the catalyst composite although suitable metals include palladium, ruthenium, nickel, zinc, tin and cobalt, with palladium being particularly advantageous. Generally, the amount of hydrogenation metal present in the catalyst composite is preferred to be between about 0.05 and about 10 wt %, such as between about 0.1 and about 5 wt %, of the catalyst composite. In one embodiment, where the molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal is present in the composite catalyst such that at least 50 wt %, for example at least 75 wt %, and particularly preferably substantially all (eg at least 95, 98 or 99 wt %) or even 100 wt % of the hydrogenation metal is supported on the inorganic oxide. This is conveniently achieved by depositing at least part of the hydrogenation metal on the inorganic oxide before the metal-containing inorganic oxide is composited with the molecular sieve. If necessary, additional hydrogenation metal can subsequently be deposited on the resultant catalyst composite. Typically, the catalyst composite is produced by co-pelletization, in which a mixture of the molecular sieve and the inorganic oxide are formed into pellets at high pressure (generally about 350 to about 350,000 kPa), or by co-extrusion, in which a slurry of the molecular sieve and the inorganic oxide, optionally together with a separate binder, are forced through a die.

For those embodiments that employ a binder, suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the sub-bentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain some dialkylated products, as well as unreacted aromatic feed and the desired monoalkylated species. The unreacted aromatic feed is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y or mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1.

Cyclohexylbenzene Oxidation

In a preferred embodiment, the cyclohexylbenzene produced by the process of the invention is further converted. Thus, in order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N''-trihydroxyisocyanuric acid.

These catalytic materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N''-trihydroxyisocyanuric acid is employed in an amount of from 0.0001 mol % to 15 mol %, such as from 0.001 to 5 mol %, of the cyclohexylbenzene.

Suitable conditions for the oxidation step include a temperature between about 70° C. and about 200° C., such as about 90° C. to about 130° C., and/or a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C. and/or a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species. The crude or purified cyclohexanone may itself be subjected to dehydrogenation in order to convert it to phenol. Such dehydrogenation may be performed, for example, over a catalyst such as platinum, nickel or palladium.

The following Example is given for illustrative purposes and does not limit the scope of the invention.

EXAMPLE

To illustrate the importance of the particle size of the support for the hydrogenation metal in benzene hydroalkylation, back-to-back experiments were conducted on two catalysts, designated A and B, prepared identically except for the particle size of the alumina support. Both catalysts contained 2 g of 0.3 wt % Pd supported on gamma alumina co-pelletized with 4.8 g of MCM-49 acidic alkylation catalyst. The main difference between catalyst A and catalyst B is that the former was supported on SASOL CATALOX SBa which has an average particle size of 45 μm (microns), whereas catalyst B was supported on 3 μm (micron) average particle size alumina from Alfa Aesar.

The average particle size of each of the two alumina supports was measured on a Microtrac S-3000 laser particle sizing analyzer supplied by Microtrac, Inc. of Largo, Fla., USA. Aqueous suspensions of the alumina samples were used, the suspensions being ultrasonicated in the analyzer in order to break up aggregates. A typical sample amount, automatically determined by the analyzer, was about 200 mg. The instrument employed software that reduced all particles to effective spherical diameters, and measured the particle size as mean volume (MV) diameter. Further details of the analyzer and its use may be found in "Explanation of Data Reported by Microtrac Instruments" Applications Note SL-AN-16 Rev B (Terminology, abbreviations and calculations shown in reports) by Philip E, Plantz, PhD, available from Microtrac, Inc. prior to April 2008. A discussion of mean volume diameter is contained in that document.

Each catalyst was prepared by first depositing palladium onto the alumina. The Pd-containing alumina was then added to MCM-49 to form a mixture and the mixture was then pelletized using a hand press under 136,000 kPaa for 60 seconds. The pellet was then sized to mesh openings of from 0.841 mm to 0.250 mm (20/60 mesh particles) before it was tested for its benzene hydroalkylation performance. With each catalyst, all the palladium was on the inorganic oxide.

Both catalysts were evaluated under nominally identical conditions of 150° C., 1034 kPag (150 psig) and 0.7 hr$^{-1}$ WHSV and the results are shown in Table 1. As can be seen from Table 1, the performance of catalyst B was superior to that of catalyst A. The conversion of catalyst B was significantly higher (59 versus 46 wt % conversion). Moreover, the selectivity to cyclohexane of catalyst B was outstandingly low, at 2.6%. The selectivity to methylcyclopentane (MCP) of catalyst B appears to be to be high at 1.3%, but most of the higher selectivity to MCP is due to the higher conversion. The overall selectivity of catalyst B was excellent, at 91% at nearly 59% conversion.

TABLE 1

|  | A | B |
|---|---|---|
| Catalyst |  |  |
| Alumina Support Average Particle Size, μm (microns) | 45 | 3 |
| Conversion, wt % | 46.3 | 59.3 |
| Selectivity, wt % |  |  |
| Cyclohexane | 4.5 | 2.6 |
| Cyclohexylbenzene (CHB) | 72.6 | 71.7 |
| Dicyclohexylbenzene (DCHB) | 18.5 | 19.4 |
| CHB + DCHB | 91.1 | 91.1 |
| Methylcyclopentane | 0.2 | 1.3 |
| Methylcyclopentylbenzene | 1.9 | 2.1 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing cyclohexylbenzene, the process comprising contacting benzene and hydrogen with a catalyst under hydroalkylation conditions to produce an effluent containing cyclohexylbenzene, the catalyst comprising a composite of a molecular sieve, an inorganic oxide different from the molecular sieve and at least one hydrogenation metal, wherein at least 50 wt % of the hydrogenation metal is supported on the inorganic oxide and the inorganic oxide has an average particle size less than 40 μm (microns).

2. The process of claim 1, wherein the inorganic oxide has an average particle size of from 0.01 to 30 μm.

3. The process of claim 1, wherein the inorganic oxide has an average particle size less than 20 μm.

4. The process of claim 1, wherein the inorganic oxide has an average particle size less than 5 μm.

5. The process of claim 1, wherein the inorganic oxide comprises an oxide of at least one element of Groups 2, 4, 13 and 14 of the Periodic Table of Elements.

6. The process of claim 5 wherein the inorganic oxide comprises alumina, titania or zirconia.

7. The process of claim 1, wherein at least 75 wt % of the hydrogenation metal is supported on the inorganic oxide.

8. The process of claim 1, wherein the at least one hydrogenation metal is applied to the inorganic oxide before the inorganic oxide is composited with the molecular sieve.

9. The process of claim 8, wherein the catalyst is produced by depositing the at least one hydrogenation metal on the inorganic oxide and then co-pelletizing a mixture of the metal-containing inorganic oxide and the molecular sieve.

10. The process of claim 8, wherein the catalyst is produced by depositing the at least one hydrogenation metal on the inorganic oxide and then co-extruding a mixture of the metal-containing inorganic oxide and the molecular sieve.

11. The process of claim 1, wherein the catalyst further includes a binder.

12. The process of claim 1, wherein the molecular sieve has an average pore size of at least $7 \times 10^{-10}$ m (7 Angstrom).

13. The process of claim 1, wherein the molecular sieve is selected from zeolite beta, zeolite X, zeolite Y, mordenite and a molecular sieve of the MCM-22 family.

14. The process of claim 1, wherein the molecular sieve has an X-ray diffraction pattern including d-spacing maxima at 12.4±0.25, 6.9±0.15, 3.57±0.07 and 3.42±0.07 Angstrom.

15. The process of claim 1, wherein the molecular sieve is selected from MCM-22, PSH-3, SSZ-25, ERB-1, ITQ-1, ITQ-2, MCM-36, MCM-49, MCM-56, UZM-8, and combinations of any two or more thereof.

16. The process of claim 1, wherein the molecular sieve is an aluminosilicate and the molar ratio of the aluminum in the molecular sieve to the hydrogenation metal is from 1.5 to 1500.

17. The process of claim 16 wherein the molar ratio is from 100 to 300.

18. The process of claim 1, wherein the at least one hydrogenation metal is selected from palladium, ruthenium, nickel, zinc, tin, and cobalt.

19. The process of claim 1, wherein the molar ratio of hydrogen to benzene in the contacting is in the range of from 0.15:1 to 15:1.

20. The process of claim 1, wherein the hydroalkylation conditions include a temperature of 100 to 400° C. and/or a pressure of 100 to 7000 kPaa.

21. The process of claim 1, wherein the effluent also contains dicyclohexylbenzene and at least part of the dicyclohexylbenzene is contacted with benzene under transalkylation conditions to produce further cyclohexylbenzene.

22. A method for coproducing phenol and cyclohexanone, the method comprising producing cyclohexylbenzene by the process of claim 1, oxidizing the cyclohexylbenzene to produce cyclohexylbenzene hydroperoxide and cleaving the cyclohexylbenzene hydroperoxide to produce phenol and cyclohexanone.

23. The method of claim 22, further comprising dehydrogenating the cyclohexanone to form further phenol.

24. A process for producing cyclohexylbenzene, the process comprising contacting benzene and hydrogen with a catalyst under hydroalkylation conditions to produce an effluent containing cyclohexylbenzene, the catalyst comprising a composite of a molecular sieve, an inorganic oxide different from the molecular sieve and at least one hydrogenation metal, wherein at least 50 wt % of the hydrogenation metal is supported on the inorganic oxide and the inorganic oxide has an average particle size less than 40 μm (microns) wherein the molecular sieve is selected from MCM-22, PSH-3, SSZ-25, ERB-1, ITQ-1, ITQ-2, MCM-36, MCM-49, MCM-56, UZM-8, and combinations of any two or more thereof.

25. A process for producing cyclohexylbenzene, the process comprising contacting benzene and hydrogen with a catalyst under hydroalkylation conditions to produce an effluent containing cyclohexylbenzene, the catalyst comprising a composite of a molecular sieve, an inorganic oxide different from the molecular sieve and at least one hydrogenation metal, wherein at least 75 wt % of the hydrogenation metal is supported on the inorganic oxide and the inorganic oxide has an average particle size average particle size of from 0.01 to 30 μm (microns).

* * * * *